United States Patent [19]

Dykes et al.

[11] Patent Number: 5,710,378
[45] Date of Patent: Jan. 20, 1998

[54] INSPECTION TOOL FOR DETECTING CRACKS IN JET PUMP BEAMS OF BOILING WATER REACTOR

[75] Inventors: Edward Ray Dykes, San Jose; Yehuda Krampfner, Pleasanton; David Lee Richardson, Los Gatos; Michael Edward Mosseau, Mountain View; Gunnar Viggo Vatvedt, Los Gatos, all of Calif.

[73] Assignee: General Electric Company, San Jose, Calif.

[21] Appl. No.: 414,270

[22] Filed: Mar. 31, 1995

[51] Int. Cl.⁶ .................. G01N 27/90; G01N 29/04
[52] U.S. Cl. .................. 73/601; 73/621; 73/640; 324/262; 376/249
[58] Field of Search .................. 73/601, 621, 622, 73/637, 640; 324/262, 226, 238; 376/249

[56] References Cited

U.S. PATENT DOCUMENTS

| | | | |
|---|---|---|---|
| 4,383,448 | 5/1983 | Fujimoto et al. | 73/637 |
| 4,387,598 | 6/1983 | Jamieson et al. | 73/640 |
| 4,394,345 | 7/1983 | De Briere et al. | 376/245 |
| 4,474,064 | 10/1984 | Naruse et al. | 73/640 |
| 4,870,970 | 10/1989 | Gray et al. | 73/620 |
| 5,009,105 | 4/1991 | Richardson et al. | 73/621 |
| 5,334,934 | 8/1994 | Vierd | 324/262 |
| 5,481,916 | 1/1996 | Macecek et al. | 73/601 |
| 5,535,628 | 7/1996 | Rutherford | 73/622 |

Primary Examiner—John E. Chapman
Attorney, Agent, or Firm—James E. McGinness; Dennis M. Flaherty

[57] ABSTRACT

An integrated apparatus for inspecting the arms of jet pump beams using eddy current technology, while also scanning the borehole region using ultrasound technology. In order to inspect the jet pump beam arms, a special scanner is required to properly move an eddy current coil in two dimensions over the complex machined surface on top of the arms. The scanner has two axes of motion and can perform a raster scan in either direction. The inspection payload, an eddy current probe, moves the length of the scanning axis and then the payload is indexed (i.e., moved a small distance) along the indexing axis. The payload is then moved smoothly back along the length of the scanning axis. Data is collected only during motion along the scanning axis. The scanner has a unique curved track design for maintaining the orientation of the eddy current probe perpendicular to the inspection surface. It allows inspecting the top flat surface and the curved edges of the jet pump beams. The eddy current probe is mounted on a movable carriage which rolls along the curved track via two wheels which move along two different curves having the same radius, but different arc lengths.

14 Claims, 7 Drawing Sheets

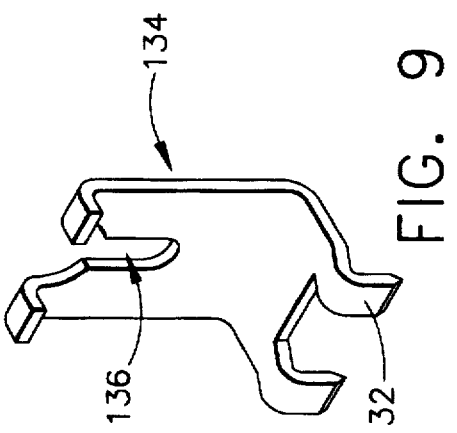
FIG. 8C
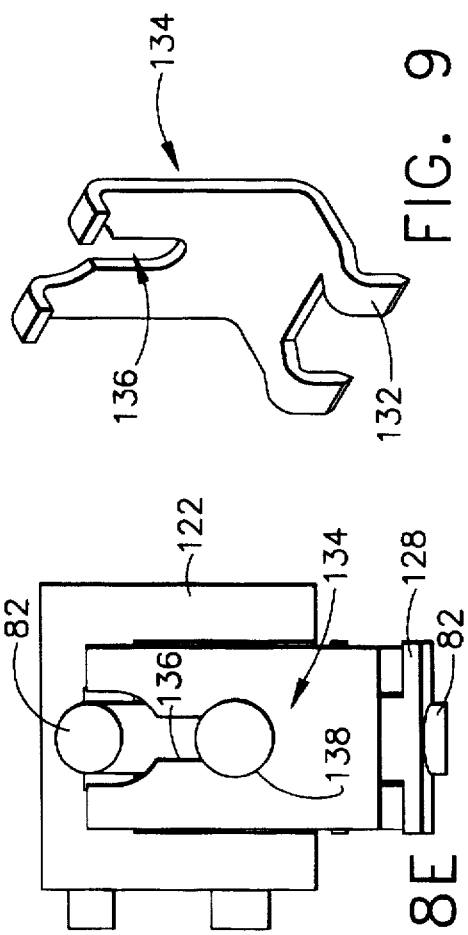
FIG. 9
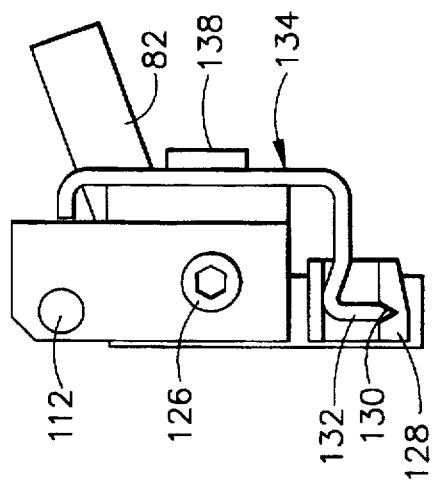
FIG. 8B
FIG. 8E
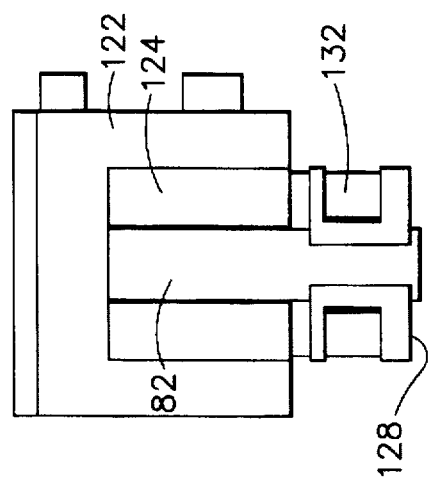
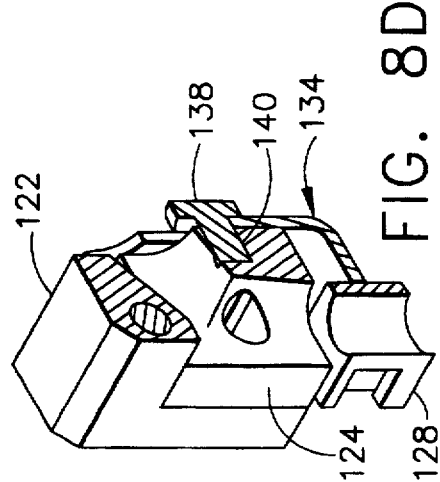
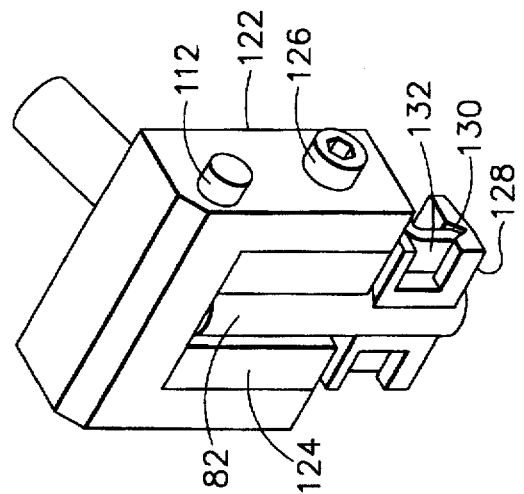
FIG. 8A
FIG. 8D

5,710,378

INSPECTION TOOL FOR DETECTING CRACKS IN JET PUMP BEAMS OF BOILING WATER REACTOR

FIELD OF THE INVENTION

This invention generally relates to the maintenance of a light-water nuclear reactor. In particular, the invention concerns the inspection of jet pump beams in the jet pump assemblies of boiling water reactors.

BACKGROUND OF THE INVENTION

In a conventional BWR, the core of nuclear fuel is cooled by water. A coolant recirculation system provides the forced convection flow through the core necessary to attain the required power density. A portion of the water is sucked from the lower end of the downcomer annulus via a recirculation water outlet and forced by a centrifugal recirculation pump into jet pump assemblies via recirculation water inlets.

A conventional jet pump assembly comprises a pair of inlet mixers 10 (see FIG. 1). Each inlet mixer has an elbow 14 welded thereto which receives pressurized driving water via an inlet riser 12. Each inlet mixer is clamped to the inlet riser 12 by a pair of transition pieces 16 and a jet pump beam 18 (see FIG. 2). Each transition piece 16 has a U-shape, with the tips of the legs of the upside-down U-shape being welded to the upper end of the inlet riser. In this position, the base of the U-shape is horizontal. The horizontal member of each transition piece 16 forms a lock post 20 for holding down a respective end of the jet pump beam 18 when the latter is in a locking position as shown in FIG. 2.

The jet pump beam 18 has a vertical threaded bore 21 which receives the threaded shaft 22b of a beam bolt 22. The beam bolt 22 has a head 22a at one end and a convex spherical thrust surface 22c at the opposite end. An annular slot 24 is formed between threaded shaft 22b and thrust surface 22c of beam bolt 22. The bolt head 22a has a cross-sectional shape which may be hexagonal or any other suitable geometry. The thrust surface 22c seats on a concave washer 28 at the bottom of a circular cylindrical recess 26 in the support block 14a. As the beam bolt is tensioned by remote manipulation of bolt head 22a, the thrust surface 22c bears against washer 28 with increasing force. The jet pump beam 18 presses against the lock posts 20 with equal and opposite force. As a result, the downward bearing force of thrust surface 22c holds the inlet mixer assembly in place. Thus, when the jet pump beam 18 is in the locking position, the associated elbow 14 is held down by the pair of transition pieces 16 via jet pump beam 18 and thrust surface 22c.

In the locking position, beam bolt 22 is secured against turning by a sleeve lock or keeper 34 tack-welded onto a weld plate 36, which is attached to the jet pump beam 18 by screws (not shown). A retainer clip 30 is secured to the support block 14a by a retainer bolt 32. Retainer clip 30 has a pair of arms which intersect the annular slot 24.

The static and dynamic load on jet pump beams, including vibrations imposed during reactor operation, has been found to cause, in some instances, beam cracking that begins in the upper central portion 18b of the beams. Cracking in a jet pump beam threatens the release of the pipe elbow from its normal position, which would impair proper jet pump operation. Accordingly, it is desirable to determine the physical integrity of jet pump beams on a regular basis.

During regular maintenance of the jet pump assemblies of a BWR, the jet pump beam and bolt assembly is ultrasonically inspected for potential cracking conditions. There are two areas on a jet pump beams where failures have occurred due to intergranular stress corrosion cracking (IGSCC): 1) in the ligaments in the raised central portion 18b adjacent to the center borehole 21, where a crevice exists between the bolt and the threaded hole; and 2) on the arms 18a. There are two arms on each jet pump beam, and both must be inspected. The highest stress area is on the top of the arms, and in the transition zone T with the machined radius.

U.S. Pat. No. 4,394,345 disclosed ultrasonic testing methods for examining the upper part of the ligament volumes adjacent to the bore hole, in the region where cracking initiates. However, that patent did not disclose any method for detecting cracks in the jet pump beam arms. Accordingly, an apparatus which is capable of inspecting both the borehole region and the arms of a jet pump beam for the presence of cracks would be a significant advancement in the state of the art.

SUMMARY OF THE INVENTION

The present invention is an integrated apparatus for inspecting the arms of the jet pump beams using eddy current technology, while also examining the threaded bore region using ultrasound technology. In order to inspect the jet pump beam arms, a special scanner is required to properly move an eddy current coil in two dimensions over the complex machined surface on top of the arms. Alternatively, an eddy current probe having an array of coils which are multiplexed while the probe is held stationary can be used to scan the machined surface. As used herein, the term "scanning" means both physical movement of an eddy current probe and multiplexing an array of coils incorporated in an eddy current probe which is held stationary.

The scanner in accordance with a preferred embodiment of the invention has two axes of motion. One axis of motion (the Y axis) is parallel to the major axis (i.e., long axis) of the jet pump beam. The other axis (the X axis) is perpendicular to the major axis, and parallel to the minor axis of the jet pump beam. The scanner can perform a raster scan in either direction, with the scanning direction either parallel or perpendicular to the major axis. In a raster scan, one axis is the indexing axis and the other axis is the scanning axis. The inspection payload, an eddy current probe, moves the length of the scanning axis and then the payload is indexed (i.e., moved a small distance) along the indexing axis. The payload is then moved smoothly back along the length of the scanning axis. Data may be acquired bidirectionally, i.e., during motion in both directions of the scanning axis, or unidirectionally, i.e., during motion in only one direction. For unidirectional data collection, the scanner will move the payload the full distance while collecting data, and will then retract it back to the original position without taking data before the scanner is incremented again along the index axis.

The system is an integrated assembly, consisting of ultrasound transducers for ultrasonic testing in accordance with U.S. Pat. No. 4,394,345 plus two eddy current scanners. In accordance with the preferred embodiment of the invention, the system uses two eddy current scanning subassemblies, one for each arm, to enable a complete examination with only one installation of the underwater tool. The use of two eddy current scanners to scan both arms simultaneously enables the inspection to be performed at high speed. Alternatively, a configuration having only a single eddy current scanner can be used to scan one jet pump beam arm at a time.

The main body of the tool is a single-piece fixture for the ultrasonic testing portion of the inspection. This is an improvement over the tool disclosed in U.S. Pat. No. 4,394,345. In accordance with the preferred embodiment of the present invention, a single aluminum block holds both ultrasonic transducers on one side of the jet pump beam. Two of these blocks are used, one for each side, and held together by a structural beam extending across the width of the tool. No mounting adjustments are necessary for these ultrasonic transducers, i.e., they are inserted and locked into place using set screws. In contrast, the prior art tool had multiple pieces requiring an alignment procedure prior to every inspection. The one-piece design in accordance with the present invention eliminates the alignment process, thereby simplifying the ultrasonic examination and improving its reliability.

In accordance with the preferred embodiment of the invention, a scanner having only two axes of motion accomplishes all of the raster scanning motion necessary for covering the complex surface on the arms of the jet pump beam. The scanner has a unique curved track design for maintaining the orientation of the eddy current probe perpendicular to the inspection surface. It allows inspecting the top flat surface and the curved edges of the jet pump beams. The track is specially shaped along the X axis. The eddy current probe is mounted on a movable carriage which rolls along the curved track via two wheels. To ensure that the eddy current probe is always held perpendicular to the inspection surface, the two wheels on the carriage holding the probe must move around the corner along two different curves. Both curves have the same radius, but different arc lengths. Without this novel track arrangement, three or more axes of motion would be required to properly manipulate the eddy current probe.

In accordance with another feature of the invention, a dual-coil eddy current probe is used. One coil is the test coil and the other coil is the reference. The system can also use a single-coil probe, in which case the reference coil is located near the eddy current instrument and not in the probe. The eddy current probe is mounted in a special assembly with a low pivot in order to allow the necessary motion to follow the contours of the inspection surface.

In accordance with a further feature of the preferred embodiment, Hall effect sensors are used for limit switches. Two Hall effect sensors are located on the X axis, one at each end. Magnets are mounted on the probe holder to actuate the proximal Hall effect sensor when a limit position is reached.

The tool in accordance with the invention is able to inspect the arms and threaded borehole region on a jet pump beam in situ to determine if IGSCC is present. One jet pump beam can be completely inspected in one setup with the tool, without rotating or otherwise repositioning the tool.

Utilizing the inspection method of the invention, a BWR can operate for longer durations without changing the jet pump beams. Without a sensitive inspection method, the jet pump beams in a BWR must be replaced on a regular basis to ensure that failure will not occur. In addition, the jet pump beam inspection tool allows sensitive evaluation of the population of jet pump beams that have been replaced in order to help evaluate the cracking problem.

BRIEF DESCRIPTION OF THE DRAWINGS

FIGS. 8A–8E are isometric, front, side, sectional isometric and rear views of the eddy current probe spring mounting assembly in accordance with the preferred embodiment of the present invention.

FIG. 9 is an isometric view of the holding spring incorporated in the eddy current probe spring mounting assembly shown in FIGS. 8A–8E.

DETAILED DESCRIPTION OF THE PREFERRED EMBODIMENTS

Figure 1:
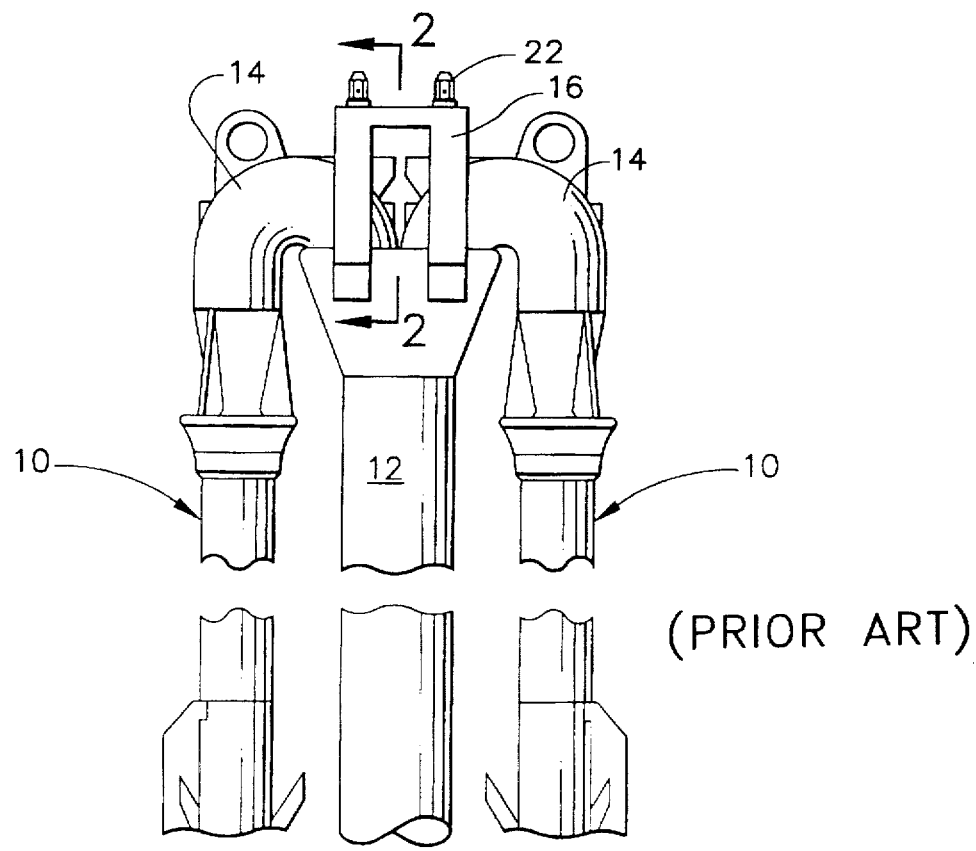
FIG. 1 is a schematic of a conventional BWR jet pump assembly.
Figure 2:
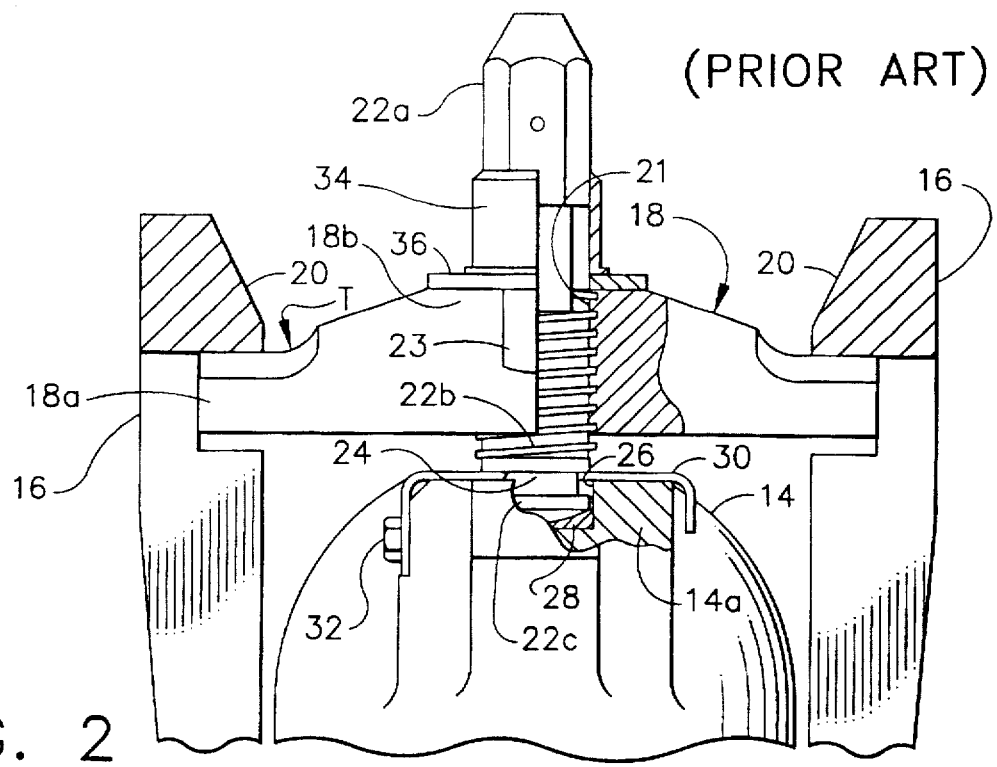
FIG. 2 is a view taken along section line 2—2 shown in FIG. 1.
Figure 3:
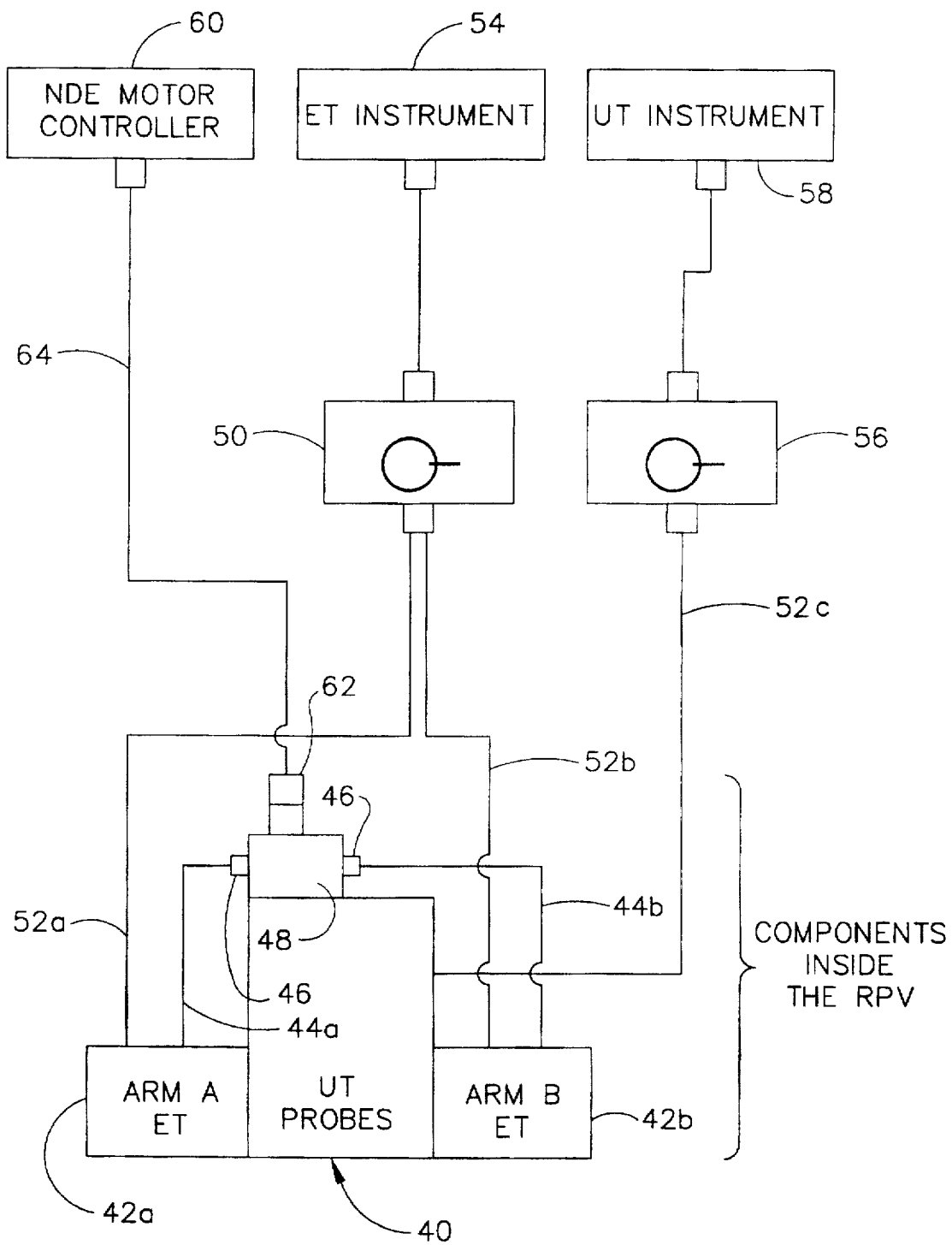
FIG. 3 is a block diagram showing the jet pump beam inspection tool system in accordance with the present invention.

The present invention combines ultrasonic detection and eddy current detection to detect cracks formed in the jet pump beams of a boiling water reactor. As seen in FIG. 3, the system comprises an ultrasonic transducer subassembly 40 for inspecting the raised central portion 18b of the jet pump beam 18 and a pair of eddy current scanning subassemblies 42a and 42b for respectively inspecting the arms 18a of the jet pump beam. This integrated assembly enables a complete examination of the jet pump beam with only one installation of the underwater tool.

The entire tool assembly is designed for underwater operation down to a depth of about 80 feet. The cables 44a and 44b for the Hall effect sensors and the stepper motors insert through waterproof fittings 46 into a junction box 48 mounted on the ultrasonic transducer subassembly 40. Power is supplied to the motor drive cables by a motor controller 60 which connects to a waterproof connector 62 on the junction box 48 via a waterproof cable 64, as shown in FIG. 3. The motors and sensors (not shown in FIG. 3) are water-proofed using potting compound. The stepper motors have integral reduction gears. The power output shafts of the motors are sealed against water intrusion using an O-ring. All cables lead to the junction box 48, which has a pressure fitting. Since all cables lead to the junction box, the air spaces inside all cables on the tool and inside all motors vent to the junction box. Consequently, leak testing for all waterproof components may be accomplished using a vacuum pump connected to the pressure fitting on the junction box. This single pressure fitting can also be used to pressurize the tool and equalize the pressure for all cables and motors on the tool, if necessary to prevent leaks.

The eddy current probes are connected to an eddy current probe manual selection switch 50 via coaxial cables 52a and 52b. Switch 50 selectively connects one of two eddy current probes to the eddy current instrument 54. The ultrasonic transducers are connected to an ultrasonic transducer manual selection switch 56 via respective coaxial cables 52c (only one of which is depicted in FIG. 3). Depending on the detection mode selected by the operator, switch 56 selectively connects one (for pitch-echo mode) or two (for pitch-catch mode) ultrasonic transducers to the ultrasonic instrument 58. The ultrasonic instrument 58 is a conventional instrument comprising a signal generator or ultrasonic transmitter, a receiver and a visual display.

Figure 4A:
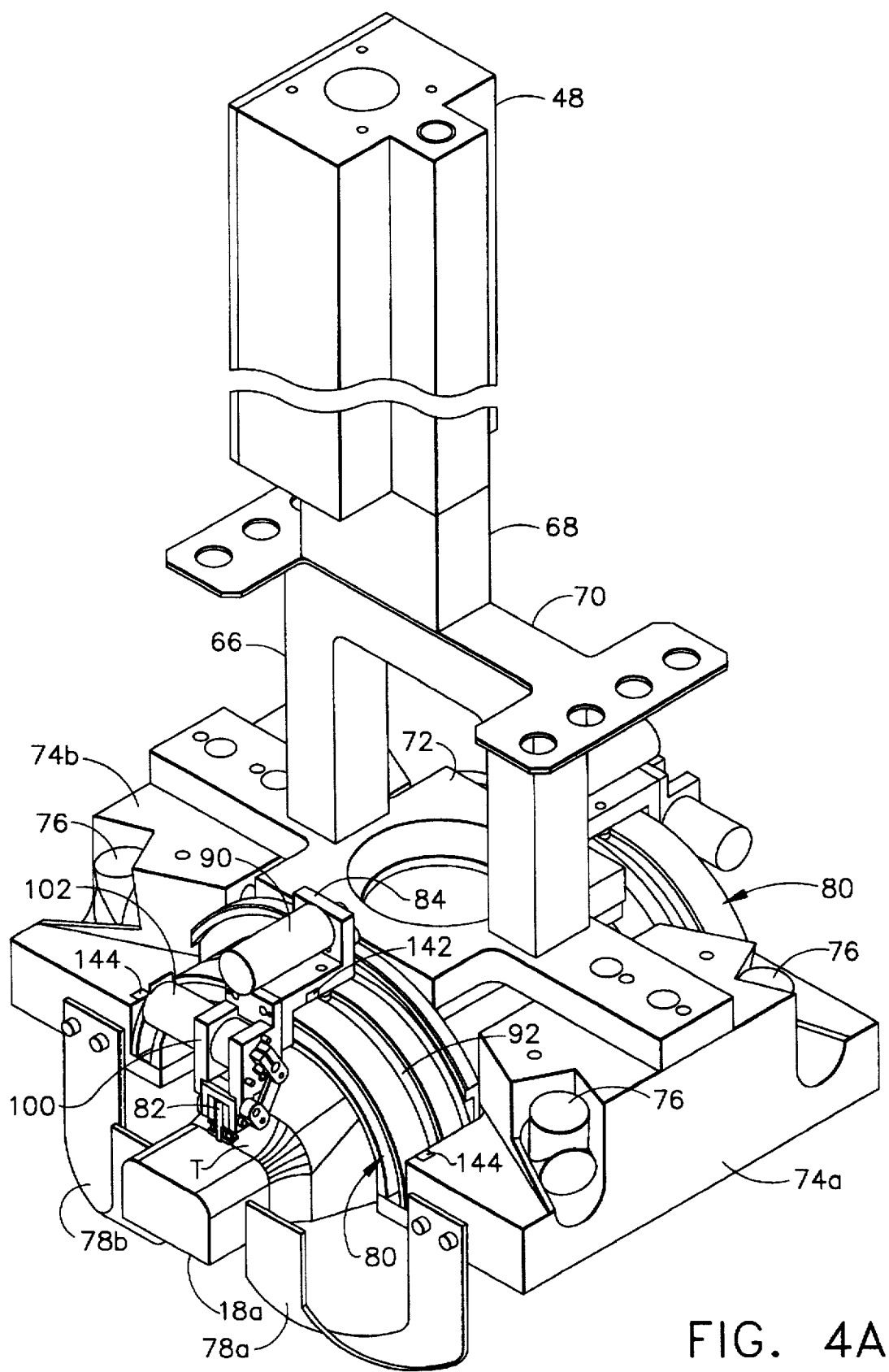
FIG. 4A is an isometric view of a jet pump beam inspection tool in accordance with a preferred embodiment of the invention.

In operation, a technician lowers the tool onto the jet pump beam in the stored position using a service pole (not shown). As seen in FIG. 4A, the tool comprises a U-shaped bail 66 which couples to the end connector (not shown) of the service pole. The junction box 48 is supported in an upright position by a support post 68, which is secured to the bail 66 with a mounting plate 70 sandwiched therebetween. The mounting plate 70 has two sets of openings for receiving respective fittings (not shown) which secure the coaxial cables (52a, 52b and 52c in FIG. 3). The bail 66 in turn is attached to a base 72 which supports a pair of ultrasonic transducer holders 74a and 74b at respective ends thereof. Each holder 74a and 74b holds a pair of ultrasonic transducers 76. The ultrasonic transducers mounted in holder 74a oppose the ultrasonic transducers mounted in holder 74b so that transducers on opposing holders can be operated in a "pitch-catch" mode, if desired. The holders 74a and 74b are separated by a distance slightly greater than the maximum width of the jet pump beam 18 to allow the jet pump beam to nest in the cavity therebetween. The base 72 is provided with a circular opening for passage therethrough of the beam bolt 22 when the tool is mounted on the jet pump beam assembly. Also, each holder has a recessed portion for placement on a respective trunnion 23 on the jet pump beam 18. In addition, the end faces of each holder 74a and 74b have respective flexible locating bands 78a and 78b which guide the tool into the correct position for inspection by means of opposing abutment with jet pump beam arms 18a.

In accordance with the preferred embodiment of the invention, a pair of curved tracks 80 are secured to the ultrasonic transducer support assembly. Each track supports and guides a rolling carriage which carries a respective eddy current probe 82 for inspecting the machined transition portion T of a respective jet pump beam arm 18a. In the alternative, only one eddy current probe subassembly is provided for scanning the jet pump beam arms in sequence, which arrangement requires two separate tool installations.

As seen in FIGS. 4A, 5 and 6A–6C, the rolling carriage comprises a bracket 84 having rollers which ride in respective grooves in track 80. The grooves include an upper groove 86 which guides a single roller 88 supported on the upper leg of bracket 84; a middle groove 92 which guides a pair of rollers 94 pivotably mounted on the middle leg of bracket 84; and a lower groove 96 having inner and outer guide surfaces 96a and 96b which respectively guide rollers 8b, which are in turn pivotably mounted on the lower leg of bracket 84. Abutment of the guide surfaces with the peripheral surfaces of the rollers prevents disengagement of the rolling carriage from the track.

Figure 5:
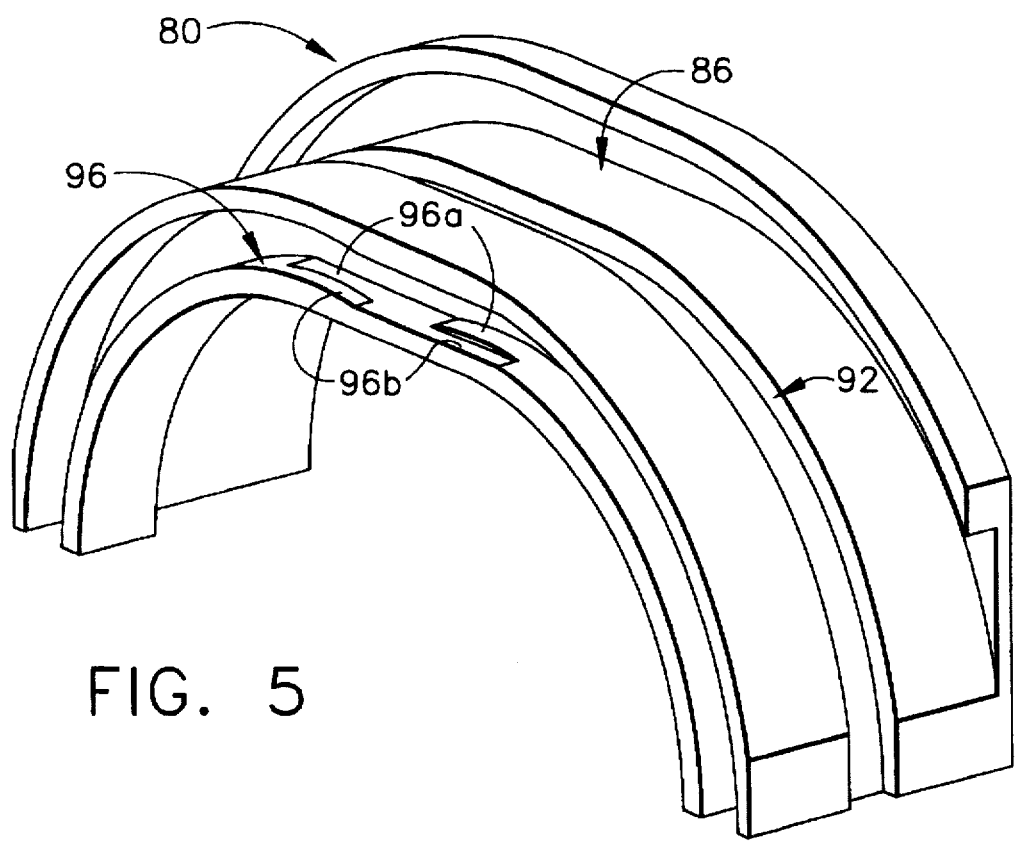
FIG. 5 is an isometric view of a curved track incorporated in the jet pump beam inspection tool depicted in FIG. 4A.
Figure 6A:
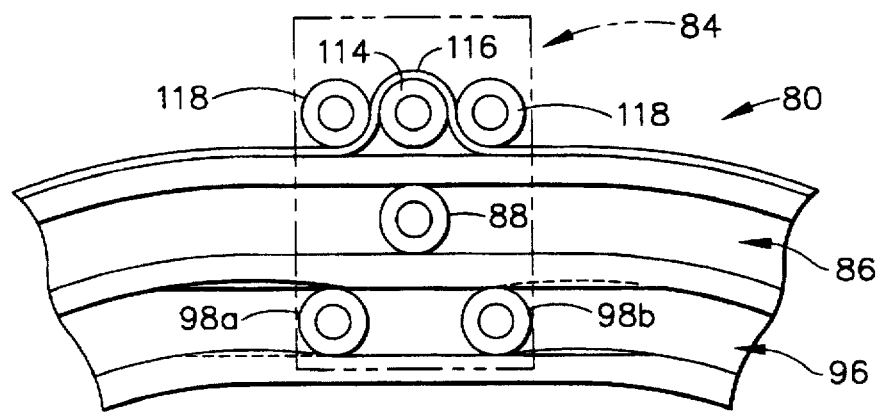
FIGS. 6A, 6B and 6C are schematic diagrams depicting three positions of a carriage which rolls along the curved track shown in FIG. 5 during eddy current scanning and which supports an eddy current probe (shown in FIG. 7).
Figure 6B:
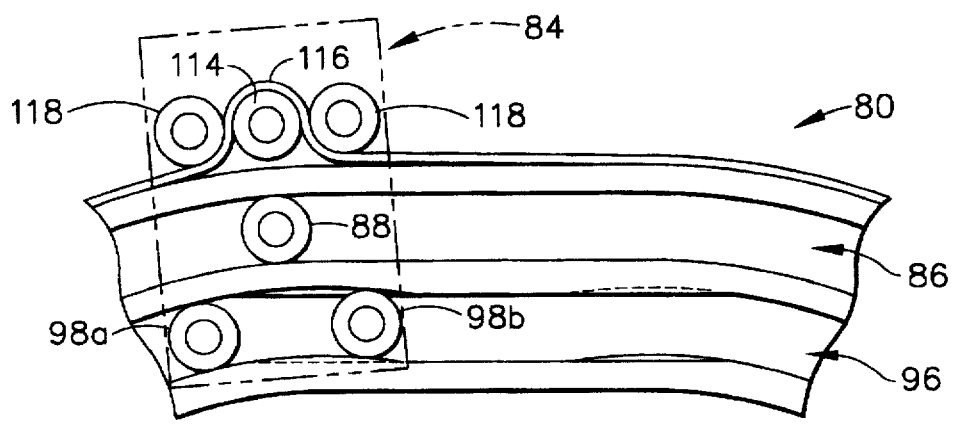
Figure 6C:
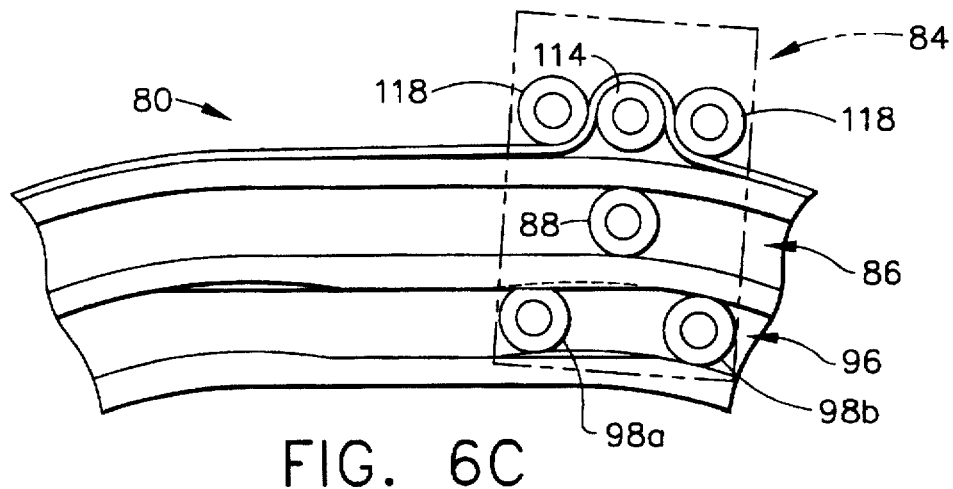

To ensure that the eddy current probe 82 is always held perpendicular to the inspection surface, the rollers 98a 98b move around the corner of the track 80 along the two different curves. As best seen in FIG. 5, each of inner and outer lower guide surfaces 96a and 96b consists of a first arcuate portion of predetermined radius and first arc length, a second arcuate portion of said predetermined radius and a second arc length less than the first arc length, and a straight portion connecting the first and second arcuate portions. Thus, the adjacent arcuate portions of inner and outer lower guide surfaces 96a and 96b have the same radius, but different arc lengths. The axes of rotation of rollers 98a and 98b are parallel and separated by a distance equal to the length of the straight section of guide surface 96a which is adjacent to an arcuate section of second guide surface 96b. As seen in FIGS. 6A–6C, the different arc lengths ensure that when roller 98a is riding on the arcuate portion of inner lower guide surface 96a, the other roller 98b is riding on the corresponding arcuate portion of outer lower guide surface 96b, and that when roller 98a is riding on the straight portion of inner lower guide surface 96a, roller 98b is riding on the straight portion of outer lower guide surface 96b.

Travel of the rolling carriage along the track is driven by a stepper motor 90 mounted thereon. A pinion gear 114 is mounted on the end of the motor drive shaft. The teeth of the pinion gear 114 mesh with a flexible toothed belt 116 made of rubber. The ends of toothed belt 116 are anchored at opposite sides of the track, while the intermediate portion of the belt is threaded under a pair of idler rollers 118 and over the pinion gear 114. The idler rollers are pivotably mounted on the upper leg of bracket 84. When the stepper motor 90 is actuated, the pinion gear rotates through a predetermined angular interval. At all times during this rotation, a predetermined arc length of the toothed peripheral surface of pinion gear 114 is intermeshed with a corresponding length of the anchored flexible toothed belt 116 held against the gear by the idler rollers 118. Thus, rotation of the pinion gear pulls the rolling carriage along the toothed belt, causing the carriage to roll along the track in a direction determined by the direction in which pinion gear 114 rotates.

Each bracket 84 has a pair of magnets 142 mounted on opposing sides of the bracket. At the limits of rolling carriage travel along the X axis, respective Hall effect sensors 144 are mounted on the ultrasonic transducer holders. Each track has two Hall effect sensors associated therewith, one Hall effect sensor at each end of the track. Each Hall effect sensor is positioned to be actuated by the proximal magnet 142 when the rolling carriage reaches the corresponding predetermined limit of travel. Thus, the Hall effect sensors act as limit switches.

Figure 4B:
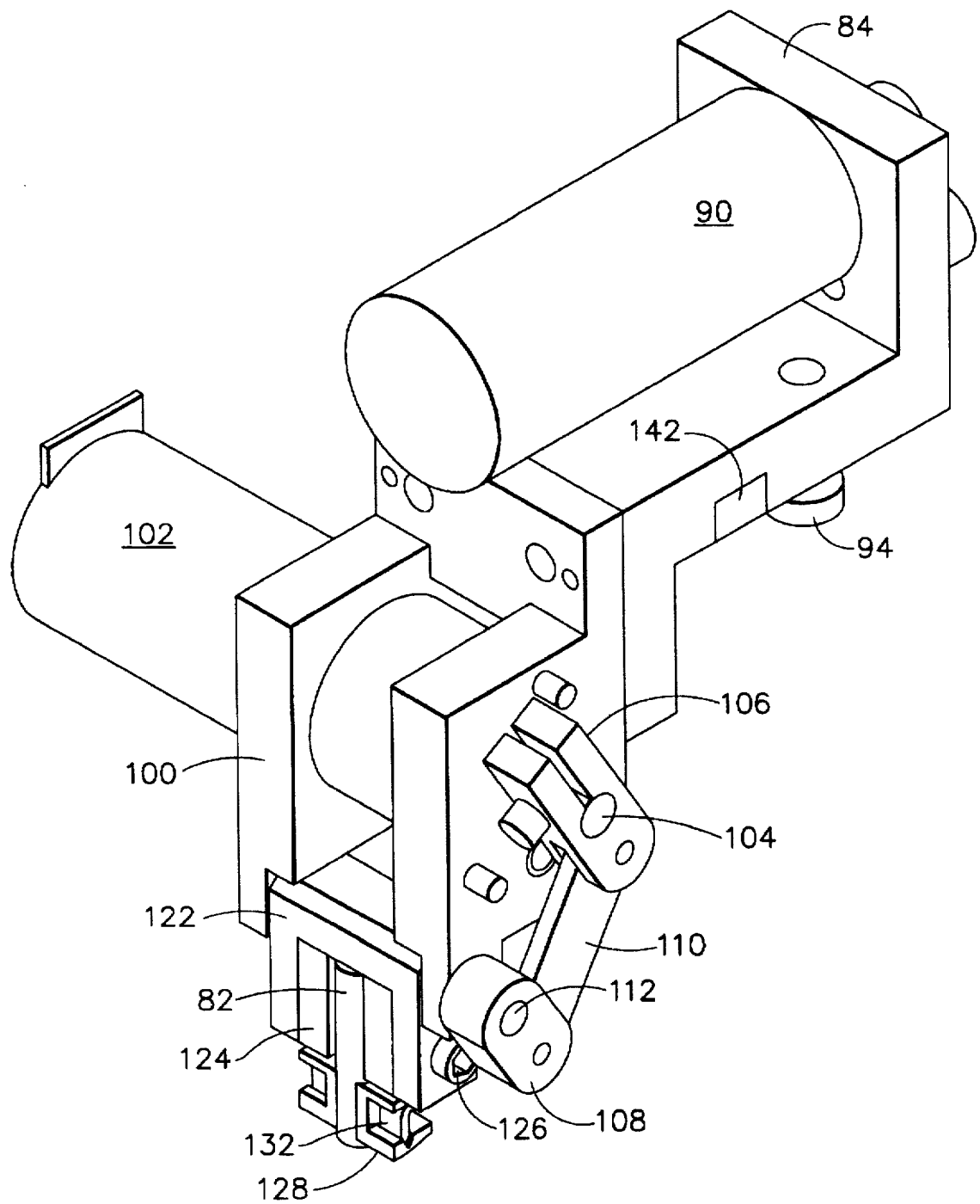
FIG. 4B is an isometric view of the rolling carriage incorporated in the jet pump beam inspection tool depicted in FIG. 4A.

Referring to FIG. 4B, the rolling carriage further comprises a bracket swivel 100 which is attached to the lower leg of bracket 84. Bracket swivel 100 supports a stepper motor 102 having a motor drive shaft 104. A motor drive crank 106 is mounted on the end of motor drive shaft 104 and is rotatable therewith. The end of motor drive crank 106 is coupled to one end of a sensor drive crank 108 via a sensor pivoting link 110. The other end of sensor drive crank 108 is mounted on the end of a sensor drive shaft 112 which is pivotably mounted in bracket swivel 100. Thus, in response to actuation of drive motor 102, sensor drive shaft 112 can be rotated.

An eddy current probe spring mounting assembly 120, shown in FIGS. 8A–8E, is mounted on the sensor drive shaft 112 for rotation therewith via a pivot 122. The pivot 122 has a generally U-shaped configuration. Each leg of the U-shaped pivot 122 is connected to a corresponding side of a probe holder 124 via respective screws 126. As best seen in FIG. 8D, the probe holder 124 has an angled recess formed therein for loosely receiving and guiding the eddy current probe 82. The probe 82 is movable relative to the probe holder 124, but the probe holder allows the probe to move (i.e., translate and rotate) only in a plane perpendicular to the sensor drive shaft 112.

Figure 7:
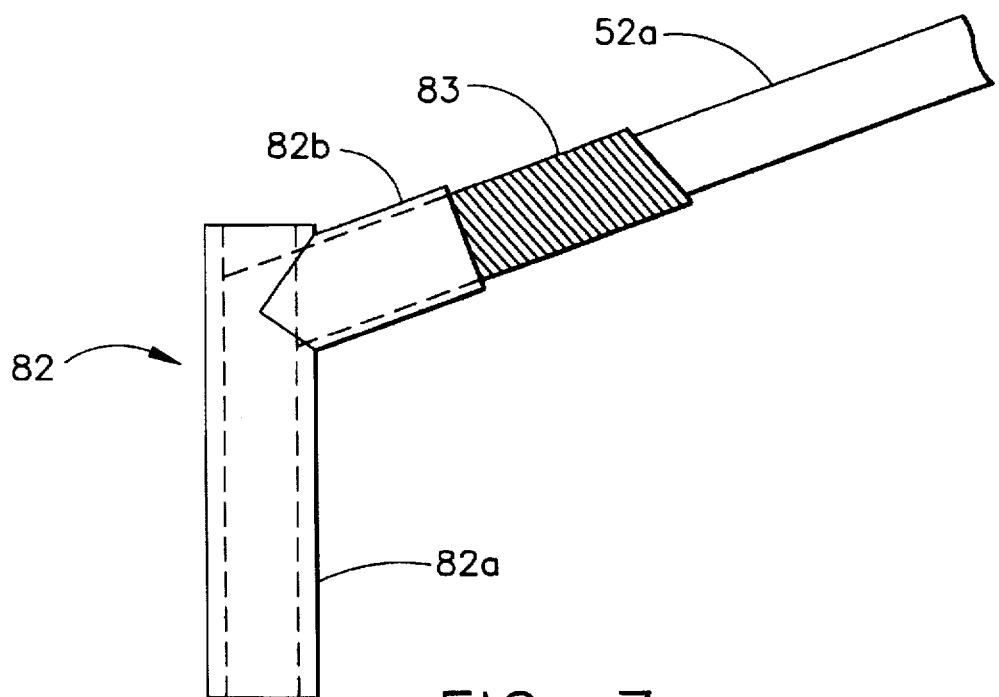
FIG. 7 is an elevational view of an eddy current probe incorporated in the jet pump beam inspection tool shown in FIG. 4A.

Referring to FIG. 7, the probe 82 comprises a pair of circular cylindrical metal (e.g., Type 440 hardened stainless steel) housings 82a and 82b joined at an angle of 70°. The housing 82a houses a ferrite core having two coils of wire wound around the core. The housing 82b houses the end of the coaxial cable 52a or 52b, which cable is electrically connected to the wires wound around the ferrite core. A spring 83 wound around the cable and attached to the end of housing 82b serves to resist flexing of the cable at the point where it enters housing 82b.

Referring to FIG. 8A, a probe clamp 128 is attached to a bottom portion of housing 82a of probe 82. The probe clamp 128 has a recess in the shape of a section of a circular cylinder of radius approximately equal to the radius of the housing 82a. The tight fit between the bottom portion of housing 82a and the recess of probe clamp 128 allows the latter to clamp securely onto the probe.

The probe clamp 128 is further provided with a pair of grooves 130, visible in FIGS. 8A and 8C, which have a V-shaped cross section. Grooves 130 are located respectively on opposing sides of the clamped portion of probe 82. Each groove 130 receives the tip of a respective support arm 132 of a spring mounting plate 134 (shown in isolation in FIG. 9). The tip of each support arm 132 has a V-shaped cross section with an apex angle equal to the angle of groove 130. The spring plate 134 is made of a resilient material, such as beryllium copper.

As seen in FIGS., the spring plate 134 has a slot 136 through which the threaded shaft of a screw 138 passes. The threaded shaft of screw 138 threadably engages a threaded bore 140 in the probe holder 124. In the tensioned state, the screw 138 secures the body of spring plate 134 relative to the probe holder 124, while allowing the arms 132 to flex about an axis parallel to the sensor drive shaft 112. The support arms 132, when installed in the position shown in FIG. 8C, will resiliently support the probe clamp 128 and eddy current probe 82 attached thereto. This spring mounting allows the tip of the eddy current probe to be pressed against the inspection surface with preload. Subsequent flexing of the spring arms allows the probe tip to follow local variations in the surface contour of the machined transition zone T of the jet pump beam during scanning and indexing, maintaining the ferrite core in a generally perpendicular position relative to the inspected surface area.

Preferably, junction box 48, bail 66, support post 68, base 72, ultrasonic transducer holders 74a and 74b, tracks 80, bracket 84, bracket swivel 100, cracks 106 and 108, pivot 122, probe holder 124 and probe clamp 128 are all made of aluminum to minimize the weight of the inspection tool.

The inspection tool is maneuvered into position so that it straddles the jet pump beam 18, as depicted in FIG. 4A. In particular, notches (not shown) in the ultrasonic transducer holders the trunnions 23 on the beam 18. In this manner, the four ultrasonic transducers 76 are suitably positioned relative to the jet pump beam 18 for ultrasonic examination.

To begin ultrasonic examination, the signal generator (not shown) is energized, and the manual selection switch 56 (see FIG. 3) is suitably manually set to allow the signal generator to provide an electric signal to a chosen transducer. This signal is converted into an ultrasonic signal impinging on the side of the beam 18, which refracts from a longitudinal wave into a shear wave according to Snell's law and continues on a path without reflection until a crack is met.

The switching mechanism 56 permits a selected one or two of the transducers to be operative either individually or in pairs. In the "pitch-catch" mode, two of the transducers 76 cooperate, one sending an ultrasonic signal and the other receiving it after passage along the top surface of the beam 18. Cracks in the surface of the beam inhibit a signal sent by the "pitch" transducer from substantially reaching the "catch" transducer. Whatever signal is received by the "catch" transducer is shown on the visual display of the UT instrument 58, permitting an indication of the position and extent of a crack. In the "pulse-echo" mode of operation, the selected one of the transducers both sends and receives ultrasonic signals. A return signal is received only when the transmitted signal is substantially reflected from a crack.

In contrast to the ultrasonic transducers, which are stationary, the eddy current probes 80 are independently movable to raster scan a respective jet pump beam arm 18a. In accordance with the eddy current inspection technique used in the present invention, flaws are detected by observing the amplitudes and phases of the electrical signals from the eddy current probes as they are scanned over the surfaces of the arms. Whenever a probe moves across a discontinuity in one of the arms on a jet pump beam, a characteristic signal is plotted on the display of the eddy current instrument 54. The characteristic signal for a flaw is different from the signal arising from other sources, such as probe lift-off. The phase relationship traced out on the display as the probe moves across a flaw shows a different phase relationship compared to other phenomena. This difference in phase relationships is a powerful discrimination tool, and makes this eddy current method very reliable for detecting flaws.

The length of a flaw is the most important measurement, which the eddy current probe measures very accurately. Small cracks starting at only 78 mils deep and 125 mils in length may be able to grow all the way through the arm of a jet pump beam in a single 2-year fuel cycle of a BWR. Consequently, an inspection system must be sensitive to cracks less than 78 mils deep and 125 mils long. The system of the present invention can detect cracks as small as 10 mils deep and 100 mils long, or less.

When performing an examination, the tool is lowered from the refueling platform, or other suitable structure above the reactor vessel, using poles and ropes. The bolt assembly protruding above the beam acts as a guide. The assembly is slipped into place and is maintained in its correct orientation by the protruding bolt, by the fit of the body of the tool around the sides of the beam, and by locating bands or notched end plates (optional) fitted to the arms.

Once a given jet pump beam has been tested, the technician may remove the carriage to another beam and repeat the entire operation described above. Typically, the operation is repeated approximately 20 times in each reactor, once for each jet pump beam.

In accordance with an alternative embodiment, an eddy current probe having an array of test coils can be used to scan the machined surfaces of interest. Instead of moving the probe to facilitate scanning, the probe is stationary while the array of coils are driven in sequence via a multiplexer. As used herein, the term "eddy current probe" means probes have a single test coil as well as probes having an array of test coils.

The foregoing preferred embodiment has been disclosed for the purpose of illustration. Variations and modifications of the disclosed embodiment which do not depart from the broad concept of the invention will be readily apparent to persons skilled in the design of inspection devices of the scanning variety. All such variations and modifications are intended to be encompassed by the claims set forth hereinafter.

We claim:

1. An inspection tool for detecting cracks in a structural member having a curved surface, comprising:

a support frame;

a curved track attached to said support frame;

a rolling carriage coupled to said curved track;

first drive means mounted on said carriage for driving said carriage to roll along said curved track;

a pivot pivotably mounted on said carriage;

second drive means mounted on said carriage for driving said pivot to swivel;

a crack detecting device carried by said pivot and having a tip, wherein said tip of said crack detecting device travels along a first path lying in a first plane during rolling of said carriage along said track, and said tip travels along a second path lying in a second plane perpendicular to said first plane during swiveling of said pivot, and said first drive means comprises a flexible toothed belt having ends anchored on said curved track and having teeth which face said curved track, a pinion gear rotatably mounted on said carriage and having teeth, said pinion gear being arranged between said toothed belt and said curved track such that said teeth of said pinion gear mesh with said teeth of said toothed belt, and a stepper motor mounted on said carriage and coupled to said pinion gear.

2. The inspection tool as defined in claim 1, wherein said crack detecting device comprises an eddy current probe.

3. The inspection tool as defined in claim 2, further comprising an ultrasonic transducer mounted on said support frame.

4. The inspection tool as defined in claim 1, further comprising first and second idler rollers arranged such that an intermediate portion of said toothed belt is threaded under said first and second idler rollers and over said pinion gear.

5. An inspection tool for detecting cracks in a structural member having a curved surface, comprising:

a support frame;

a curved track attached to said support frame;

a rolling carriage coupled to said curved track;

first drive means mounted on said carriage for driving said carriage to roll along said curved track;

a pivot pivotably mounted on said carriage;

second drive means mounted on said carriage for driving said pivot to swivel;

a crack detecting device carried by said pivot and having a tip, wherein said tip of said crack detecting device travels along a first path lying in a first plane during rolling of said carriage along said track, and said tip travels along a second path lying in a second plane perpendicular to said first plane during swiveling of said pivot, and said curved track comprises a first groove having first and second guide surfaces, each of said first and second guide surfaces comprising a first arcuate section having a predetermined radius and a first arc length, a straight section having one end connected to an end of said first arcuate section, and a second arcuate section having one end connected to another end of said straight section and having said predetermined radius and a second arc length longer than said first arc length, wherein said first arcuate section of said first guide surface and said second arcuate section of said second guide surface are contiguous over said first arc length, said second arcuate section of said first guide surface and said first arcuate section of said second guide surface are contiguous over said first arc length, said straight section of said first guide surface and said straight section of said second guide surface are equal in length and contiguous along only a first portion thereof, said second arcuate section of said first guide surface and a second portion of said straight section of said second guide surface being adjacent, and a second portion of said straight section of said first guide surface and said second arcuate section of said second guide surface being adjacent, said second portion of said straight section being coplanar with a chord connecting two points along said second arcuate section in each instance.

6. The inspection tool as defined in claim 5, wherein said crack detecting device comprises an eddy current probe.

7. The inspection tool as defined in claim 5, wherein said rolling carriage comprises first and second rollers arranged to roll on said first and second guide surfaces respectively, the axes of rotation of said first and second rollers being separated by a distance substantially equal to the length of said first portion of said straight section.

8. The inspection tool as defined in claim 7, wherein said curved track comprises a second groove, and said rolling carriage comprises a third roller arranged to roll along said second groove and a bracket comprising a horizontal leg, an upper vertical leg connected to one end of said horizontal leg, and a lower vertical leg connected to another end of said horizontal leg, said first and second rollers being rotatably mounted on said lower vertical leg and said third roller being rotatably mounted on said upper vertical leg.

9. The inspection tool as defined in claim 6, further comprising an ultrasonic transducer mounted on said support frame.

10. The inspection tool as defined in claim 5, further comprising a junction box mounted on said support frame and having a pressure fitting.

11. The inspection tool as defined in claim 5, further comprising a Hall effect sensor mounted on said support frame and a magnet mounted on said carriage such that said magnet activates said Hall effect sensor when said carriage reaches a limit position.

12. An inspection tool for detecting cracks in a structural member having a curved surface, comprising:

a support frame;

a curved track attached to said support frame;

a rolling carriage coupled to said curved track;

first drive means mounted on said carriage for driving said carriage to roll along said curved track;

a pivot pivotably mounted on said carriage;

second drive means mounted on said carriage for driving said pivot to swivel;

a crack detecting device carried by said pivot and having a tip, wherein said tip of said crack detecting device travels along a first path lying in a first plane during rolling of said carriage along said track, and said tip travels along a second path lying in a second plane perpendicular to said first plane during swiveling of said pivot, further comprising a spring mounting plate attached to said pivot and having first and second flexible support arms, said pivot comprising a clamp having first and second means for attaching to said first and second support arms, respectively, of said spring mounting plate, wherein said crack detecting device is held securely by said clamp in a position between said first and second support arms.

13. The inspection tool as defined in claim 12, wherein said crack detecting device comprises an eddy current probe.

14. The inspection tool as defined in claim 13, further comprising an ultrasonic transducer mounted on said support frame.

* * * * *